United States Patent
Komata et al.

(10) Patent No.: US 7,880,033 B2
(45) Date of Patent: Feb. 1, 2011

(54) PROCESS FOR PRODUCING 3,3,3-TRIFLUOROPROPIONIC ACID

(75) Inventors: Takeo Komata, Kawagoe (JP); Kenji Hosoi, Kasukabe (JP); Shinya Akiba, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 426 days.

(21) Appl. No.: 12/092,232

(22) PCT Filed: Oct. 24, 2006

(86) PCT No.: PCT/JP2006/321117

§ 371 (c)(1),
(2), (4) Date: Apr. 30, 2008

(87) PCT Pub. No.: WO2007/052492

PCT Pub. Date: May 10, 2007

(65) Prior Publication Data
US 2009/0247786 A1    Oct. 1, 2009

(30) Foreign Application Priority Data
Nov. 1, 2005 (JP) .............................. 2005-318528
Nov. 29, 2005 (JP) .............................. 2005-343357

(51) Int. Cl.
*C07C 51/16* (2006.01)
*C07C 51/235* (2006.01)
(52) U.S. Cl. ...................................... 562/531; 562/533
(58) Field of Classification Search .................. 562/531, 562/533
See application file for complete search history.

(56) References Cited

U.S. PATENT DOCUMENTS

| | | | |
|---|---|---|---|
| 2,533,172 | A | 12/1950 | McKinley |
| 2,715,144 | A | 8/1955 | Ruh |
| 5,777,184 | A | 7/1998 | Van Der Puy et al. |
| 6,111,139 | A | 8/2000 | Van Der Puy |
| 6,137,013 | A | 10/2000 | Riedel et al. |
| 2003/0114721 | A1 | 6/2003 | Roques |

FOREIGN PATENT DOCUMENTS

| | | |
|---|---|---|
| DE | 199 59 721 A1 | 6/2000 |
| JP | 63-63633 A | 3/1988 |
| JP | 11-246461 A | 9/1999 |
| JP | 2001-302582 A | 10/2001 |
| JP | 2003-522743 A | 7/2003 |
| JP | 2004-115377 A | 4/2004 |
| JP | 2004-155676 A | 6/2004 |

OTHER PUBLICATIONS

Peters, H. M. et al., "Improved Syntheses of Ethyl 3,3,3-Trifluoropropionate and 3,3,3-Trifluoropropionic Acid", Journal of Chemical and Engineering Data, vol. 16, No. 3, 1971, p. 376-377. (USA).

Khimiya Geterotsiklicheskikh Soedinenii, No. 10, 1973, p. 1321-1324. (Russia).

Wakselman, C. et al., "Synthesis of 3,3,3-Trifluoropropionic and 4,4,4-Trifluoro-2-Ketobutyric Acids", Journal of Fluorine Chemistry, vol. 21, 1982, p. 99-106. (The Netherlands).

Solberg, J. et al., "2-(2,2,2-Trifluoroethylidene)-1,3-dithianes. New Intermediates for the Preparation of CF3-Containing Compounds", Acta Chemica Scandinavica, vol. 43, 1989, p. 69-73. (Sweden).

Bouillon, Jean-Philippe et al., "Trifluoromethylation of Aliphatic Halogen Compounds", Journal of Chemical Society, Perkin Transaction 1, 1991, p. 2147-2149. (England).

Munavalli, S. et al., "Novel reactions of perfluoro-2-(trifluoromethyl)-propene", Journal of Fluorine Chemistry, vol. 63, 1993, p. 253-264. (The Netherlands).

Yamanaka, H. et al., "Preparation of Novel β-Trifluoromethyl Vinamidinium Salt and Its Synthetic Application to Trifluoromethylated Heterocycles", Tetrahedron Letters, vol. 37, No. 11, 1996, p. 1829-1832. (England).

Golding, B. T. et al., "3,3,3-Trifluoropropan-1-Ol and 3,3,3-Trifluoropropanal", Journal of Fluorine Chemistry, vol. 30, 1985, p. 153-158. (The Netherlands).

Pazenok, S. V. et al., "β-Perfluoroalkylvinyl Alkyl Ehters", Zhurnal Organicheskoi Khimii, vol. 25, No. 7, 1989, p. 1376-1380. (Soviet Union).

Popov, A. V. et al., "Reaction of N-(3,3,3-trifluoro-2-trifluoromethylprop-1-enyl)dimethylamine with MgSO4 •7H2O. Synthesis of 4,4-difluoro-5trifluoromethy1-2-(2,2,2-trifluoro-1-trifluoromethylethyl)-4H-1,3-dioxine and cis/trans-3-dimethylamino-2trifluoromethacryloyl fluoride", Izvestiya Akademii Nauk, Seriya Khimicheskaya, No. 5, 1997, p. 1069-1071. (Russia).

International Search Report dated Dec. 19, 2006 including English translation (Eight (8) pages).

Rudolph A. Abramovitch et al., "Pyridinium p-Toluenesulfonylmethylide as a Formyl Anion Equivalent", Department of Chemistry and Geology, Clemson University, Tetrahedron Letters vol. 21, No. 8, 1980.

Supplementary European Search Report dated Jul. 2, 2010 (Seven (7) pages).

*Primary Examiner*—Taylor Victor Oh
(74) *Attorney, Agent, or Firm*—Crowell & Moring LLP

(57) ABSTRACT

A benzyl vinyl ether represented by the following formula

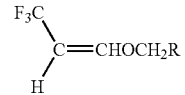

is hydrolyzed in the presence of a catalyst selected among Arrhenius acids and Lewis acids to obtain 3,3,3-trifluoropropionaldehyde. Subsequently, the 3,3,3-trifluoropropionaldehyde is oxidized with an oxidizing agent. Thus, 3,3,3-trifluoropropionic acid can be more advantageously produced than in conventional techniques from an inexpensive starting material.

7 Claims, No Drawings

PROCESS FOR PRODUCING 3,3,3-TRIFLUOROPROPIONIC ACID

TECHNICAL FIELD

The present invention relates to processes for producing 3,3,3-trifluoropropionic acid which is an useful intermediate for medicines and agricultural chemicals while being an useful synthetic intermediate or raw material for producing functional materials such as fluorine-containing polymers.

BACKGROUND OF INVENTION 3,3,3-Trifluoropropionic acid is a significantly important compound as an intermediate for medicines and agricultural chemicals, or as a synthetic intermediate or raw material for producing functional materials such as fluorine-containing polymers. Therefore, processes for producing the same have been reported variously.

In a process disclosed in Non-patent document 1, a carboxylic acid portion of monoethyl malonate ester is substituted with trifluoromethyl group by using sulfur tetrafluoride ($SF_4$). Then, monoethyl malonate ester is hydrolyzed at its ester portion, thereby producing 3,3,3-trifluoropropionic acid. A process disclosed in Non-patent document 2 is to obtain $CF_3CH_2COOSO_2OH$ upon a complex and many-stage reaction, and then hydrolyze it, thereby producing 3,3,3-trifluoropropionic acid. A process disclosed in Non-patent document 3 is to use cyclohexanecarboxylic acid and 1,1-difluoroethylene as starting materials, and to produce 3,3,3-trifluoropropionic acid through four stages.

A process disclosed in Non-patent document 4 is to use ethyl trifluoroacetate as a starting material, and to convert it to 3,3,3-trifluoropropionic acid by using mercury oxide in sulfuric acid. A process disclosed in Non-patent document 5 is to trifluoromethylate 3-bromo-1-propene with trifluoromethyl-cadmium bromide, and then to oxidize it by using potassium permanganate and crown ether, thereby producing 3,3,3-trifluoropropionic acid. In Non-patent document 6, it is reported that 3,3,3-trifluoropropionic acid is found in a mixture obtained by reacting perfluoro-2-(trifluoromethyl)propene with trifluoromethylthiocopper.

A process disclosed in Non-patent document 7 is to produce 3,3,3-trifluoropropionic acid through a radical addition of trifluoromethyl iodide to t-butyldimethylsilyl enol ether of t-butyl acetate. Patent document 1 discloses an example of producing 3,3,3-trifluoropropionic acid from dimethyl trifluoromethylmalonate by using hydrobromic acid and hydrochloric acid, and an example of producing 3,3,3-trifluoropropionic acid from 1,1,3,3,3-pentafluoro-2-trifluoropropylmethyl ether.

A technique for producing 3,3,3-trifluoropropionic acid by oxidizing 3,3,3-trifluoropropionaldehyde is exemplified by Patent document 2, in which Oxone (registered trade name) ($2KHSO_5 \cdot K_2SO_4 \cdot KHSO_4$) is employed as an oxidizing agent.

On the other hand, as a technique relating to the present invention, there are various reports concerning 3,3,3-trifluoropropionaldehyde discussed in Patent document 2 to be used as a raw material of 3,3,3-trifluoropropionic acid.

A process disclosed in Non-patent document 8 is to derive 3,3,3-trifluoro-1-propanol from 3,3,3-trifluoropropene by using mercury (II) nitrate and glacial acetic acid and then oxidize it with sodium chromate, thereby producing 3,3,3-trifluoropropionaldehyde. Additionally, a process disclosed in Patent document 3 is to react 3,3,3-trifluoropropene with water in the presence of palladium salts, thereby producing 3,3,3-trifluoropropionaldehyde. A process disclosed in Non-patent document 9 is to add trifluoromethyl iodide to ethyl vinyl ether to be hydrolyzed, thereby producing 3,3,3-trifluoropropionaldehyde. A process disclosed in Patent document 4 is to convert 1-chloro-3,3,3-trifluoropropene into 3,3,3-trifluoropropenyl acetate by using palladium salts, sodium acetate and glacial acetic acid and then hydrolyze 3,3,3-trifluoropropenyl acetate, thereby producing 3,3,3-trifluoropropionaldehyde.

A process disclosed in Patent document 5 is to hydrolyze alkyl 3,3,3-trifluoropropenyl ether by using hydroiodic acid aqueous solution, thereby producing 3,3,3-trifluoropropionaldehyde. A process disclosed in Patent document 6 is to react 1-chloro-3,3,3-trifluoropropene with metal alkoxide in an alcohol (ROH where R has a carbon number ranging from 1 to 4) so as to convert 1-chloro-3,3,3-trifluoropropene into $CF_3CH=CHOR$ or $CF_3CH(OR)_2$, and then hydrolyze it in the presence of alkanoic acid, thereby producing 3,3,3-trifluoropropionaldehyde. A process disclosed in Patent document 2 is to produce 1-chloro-3,3,3-trifluoropropyl acetate with the addition of trifluoromethanesulfonyl chloride to vinyl acetate and then hydrolyze 1-chloro-3,3,3-trifluoropropyl acetate with sulfuric acid, thereby producing 3,3,3-trifluoropropionaldehyde.

Further, a process disclosed in Non-patent document 10 is to cause a reaction on dimethyl-[1-(2-trifluoromethyl-3,3,3-trifluoropropenyl)]amine (which is a trifluoromethyl group-containing enamine) in the presence of magnesium sulfate hydrate for 28 days, thereby producing 3,3,3-trifluoropropionaldehyde.

None of these commonly known documents discusses a process for improving 3,3,3-trifluoropropionaldehyde in storage stability or a process for collecting 3,3,3-trifluoropropionaldehyde.

Patent document 1: Japanese Patent Unexamined Publication No. 2004-115377

Patent document 2: Japanese Patent Unexamined Publication No. 2003-522743

Patent document 3: Japanese Patent Unexamined Publication No. 63-63633

Patent document 4: U.S. Pat. No. 5,777,184

Patent document 5: U.S. Pat. No. 2,715,144

Patent document 6: U.S. Pat. No. 6,111,139

Non-patent document 1: Journal of Chemical and Engineering Data, Vol. 16, No. 3, p. 376-377, 1971 (United States of America)

Non-patent document 2: Khimiya Geterotsiklicheskikh Soedinenii, No. 10, p. 1321-1324, 1973 (Russia)

Non-patent document 3: Journal of Fluorine Chemistry, Vol. 21, p. 99-106, 1982 (Netherlands)

Non-patent document 4: Acta Chemica Scandinavica, Vol. 43, p. 69-73, 1989 (Sweden)

Non-patent document 5: Journal of Chemical Society, Perkin Transaction 1, p. 2147-2149 (England)

Non-patent document 6: Journal of Fluorine Chemistry, Vol. 63, p. 253-264, 1993 (Netherlands)

Non-patent document 7: Tetrahedron Letters, Vol. 37, No. 11, p. 1829-1832 (England)

Non-patent document 8: Journal of Fluorine Chemistry, Vol. 30, p. 153-158, 1985 (Netherlands)

Non-patent document 9: Zhurnal Organicheskoi Khimii, Vol. 25, No. 7, p. 1376-1380, 1989 (Soviet Union)

Non-patent document 10: Izvestiya Akademii Nauk, Seriya Khimicheskaya, No. 5, p. 1069-1071, 1997 (Russia)

SUMMARY OF INVENTION

However, hitherto known processes for producing 3,3,3-trifluoropropionic acid have disadvantages of, for example, requiring expensive materials or using a cumbersome reagent, though advantageous as far as they are conducted in a small scale.

In the process disclosed in Non-patent document 1, $SF_4$ serving as a fluorinating agent is so reactive as to be cumbersome. The processes disclosed in Non-patent documents 2, 3 and 4 have a problem of requiring a lot of stages. Further, the process discussed in Non-patent document 4 employs mercury oxide while the process discussed in Non-patent document 5 employs trifluoromethylcadmium bromide, so that these processes are limited in industrial use. The process discussed in Non-patent document 6 has a disadvantage where trifluoromethylthiocopper is hardly available and a main product is not 3,3,3-trifluoropropionic acid. The process disclosed in Non-patent document 7 requires employing an expensive trifluoromethyl iodide. The process disclosed in Patent document 1 cannot to be said to be industrially advantageous since 1,1,3,3,3-pentafluoro-2-trifluoromethylpropylmethyl ether and dimethyl trifluoromethylmalonate are expensive.

On the other hand, the process as disclosed in Patent document 2 is an advantageous process in terms of producing 3,3,3-trifluoropropionic acid, in which the raw material (i.e., 3,3,3-trifluoropropionaldehyde) is oxidized to produce 3,3,3-trifluoropropionic acid. In this process, however, a conventional technique of producing 3,3,3-trifluoropropionaldehyde as the raw material is industrially disadvantageous.

The process disclosed in Non-patent document 8 requires toxic chemicals such as mercury and chromic acid. The processes disclosed in Patent documents 3 and 4 require a large amount of expensive palladium salt. The process disclosed in Patent document 5 requires an expensive trifluoromethyl iodide. The process disclosed in Non-patent document 5 further requires hydroiodic acid which is also expensive, highly corrosive, and cumbersome. The process disclosed in Patent document 2 requires an expensive trifluoromethanesulfonyl chloride. The process disclosed in Non-patent document 10 is a rare example of conversion of trifluoromethyl group-containing enamines into 3,3,3-trifluoropropionaldehyde, but the reaction takes 28 days while a main product is not 3,3,3-trifluoropropionaldehyde.

On the other hand, the process disclosed in Patent document 6 employs 1-chloro-3,3,3-trifluoropropene as a starting material. 1-Chloro-3,3,3-trifluoropropene is converted into 3,3,3-trifluoromethyl vinyl ether (which may be hereinafter referred to as "vinyl ether") and then hydrolyzed to produce 3,3,3-trifluoropropionaldehyde, at which this process of Patent document 6 overlaps with the first and second steps of the present invention.

A process for producing "vinyl ether" is already reported in U.S. Pat. No. 2,739,987, in which "vinyl ether" can be obtained by reacting open-chain alcohols such as methanol with 1-chloro-3,3,3-trifluoropropene in the presence of bases such as KOH, as shown in a formula (a).

(a)

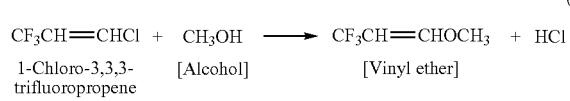

1-Chloro-3,3,3-    [Alcohol]         [Vinyl ether]
trifluoropropene

However, when the thus obtained "vinyl ether" is hydrolyzed as shown in a formula (b) in the presence of a catalyst exemplified by inorganic acids such as HCl, a target 3,3,3-trifluoropropionaldehyde is obtained only with a yield of far less than 50%.

(b)

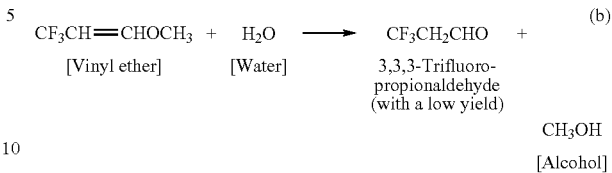

[Vinyl ether]    [Water]    3,3,3-Trifluoro-
                            propionaldehyde
                            (with a low yield)

$CH_3OH$
                                          [Alcohol]

The major reason for the low yield is that "alcohol" (which is produced as a by-product of hydrolysis) is reacted with "vinyl ether" (which is a raw material) to produce "acetal of 3,3,3-trifluoropropionaldehyde (which may be hereinafter referred to as "acetal")" as shown in a side reaction formula (c), and that the side reaction advances superiorly.

(c)

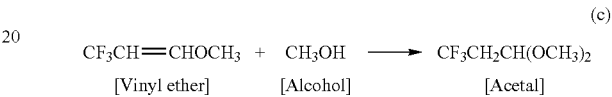

[Vinyl ether]    [Alcohol]         [Acetal]

In a case where "an excessive amount of alcohol" is used in a vinyl etherification (a) conducted prior to a hydrolysis (b) and remains in a system, the side reaction (c) further occurs remarkably so as to lower the yield of the target product substantially.

In order to solve the above problems, Patent document 5 proposes a process for hydrolyzing "vinyl ether" in such a manner as to cause "alkanoic acid serving as an acceptor for alcohols and having a carbon number ranging from 3 to 16" to coexist in the system. More specifically, it is found that, when "alkanoic acid having a carbon number ranging from 3 to 16" coexists in the hydrolysis represented by the formula (b), the by-product alcohol is caught by the alkanoic acid thereby greatly inhibiting the side reaction (c). It is disclosed that the yield of the target product is advantageously increased, more specifically that 3,3,3-trifluoropropionaldehyde is obtained from 1-chloro-3,3,3-trifluoropropene with a yield of about 70%.

However, the process of Patent document 5 employs "alkanoic acid having a carbon number ranging from 3 to 16" as "an acceptor" for alcohols and requires it in an amount equal to or larger than "vinyl ether" in mole, which causes a productivity reduction. Further, there is a disadvantage of producing alkanoic acid ester as a by-product, the alkanoic acid ester being produced in an amount equal to 3,3,3-trifluoropropionaldehyde in mole but undesired. Of these alkanoic acids, a long-chain alkanoic acid having a carbon number of not less than 6 (such as hexanoic acid) is excellent in effect of improving the yield of 3,3,3-trifluoropropionaldehyde, but expensive.

As discussed above, most of conventional processes for producing 3,3,3-trifluoropropionic acid have disadvantages, for example, of requiring a raw material unsuitable for mass synthesis. Of these conventional processes, a process for oxidizing 3,3,3-trifluoropropionaldehyde is placed as a promising process; however, it has a difficulty in efficiently producing 3,3,3-trifluoropropionaldehyde (i.e., the raw material).

Further, 3,3,3-trifluoropropionaldehyde itself is not always a stable compound and has a difficulty in a long period of storage since the purity of 3,3,3-trifluoropropionaldehyde is lowered due to formation of: 3,3,3-trifluoropropionaldehyde trimer represented by formula [7] obtained by a reaction of 3,3,3-trifluoropropionaldehyde represented by formula [2]; 3,3,3-trifluoropropionic acid represented by formula [3], obtained by oxidation of 3,3,3-trifluoropropionaldehyde; and one or more compounds having an unidentified structure (the compounds will be hereinafter defined to as "impurities"). Additionally, the once produced compounds are hard to be collected to 3,3,3-trifluoropropionaldehyde.

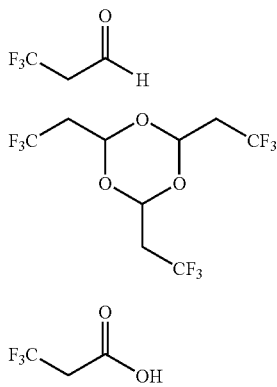

[2]

[7]

[3]

In view of the above, a large quantity of 3,3,3-trifluoropropionaldehyde is used as an industrial material so that a process which is stable and endurable against a long period of storage has been desired.

In view of the above problems, the present inventors had eagerly studied in order to find a suitable process for industrial production of 3,3,3-trifluoropropionic acid. As a result of this, it was found that 3,3,3-trifluoropropionaldehyde represented by the formula [2] is produced with a high yield when benzyl vinyl ether represented by formula [1]

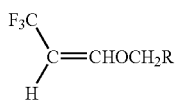

[1]

(where R is phenyl group or a phenyl group having a substitution group represented by $R^1$, where $R^1$ is a group selected from alkyl group, alkoxy group, halogen atom and nitro group) is hydrolyzed in the presence of a catalyst selected from Arrhenius acid and Lewis acid. This hydrolysis step may be hereinafter referred to as "the second step". Then, it was also found that 3,3,3-trifluoropropionic acid represented by the formula [3] can be obtained with a high yield by oxidizing the obtained 3,3,3-trifluoropropionaldehyde with an oxidizing agent thereby solving the above problems. Hereinafter, this oxidization step may be referred to as "the fourth step". The process for producing 3,3,3-trifluoropropionic acid as discussed above relates to the first aspect of the present invention.

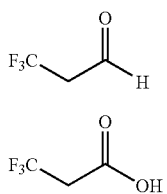

[2]

[3]

In the above-mentioned production process, a particularly important step is the hydrolysis step (or the second step). More specifically, the above-mentioned production process is characterized by using "vinyl ethers" as the raw material for the hydrolysis (or the second step), vinyl ethers being defined to have a structure of "benzyl ($RCH_2$—)". In other words, though a target 3,3,3-trifluoropropionaldehyde is produced when benzyl vinyl ether represented by the formula [1] is hydrolyzed in the presence of a catalyst selected from Arrhenius acid and Lewis acid, the present inventors have found that "acetal" is not so produced as to be expected, between benzyl alcohol ($RCH_2OH$) produced as the by-product and "benzyl vinyl ether" used as the raw material, as bellow.

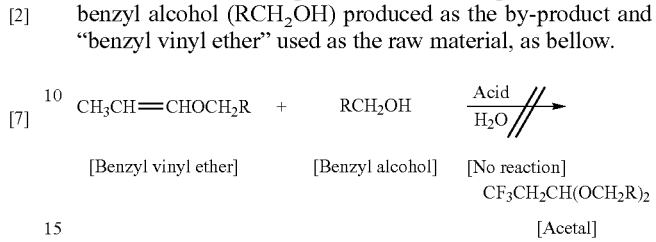

As a result of this, it is found that a large quantity of "alkanoic acid having a carbon number ranging from 3 to 16" employed in Patent document 6 as the acceptor is not needed, and additionally that the hydrolysis (or the second step) is allowed to occur with a yield of far more than 50% when "the catalytic amount of Arrhenius acid or Lewis acid" alone is used.

In addition to this, an extremely inexpensive Arrhenius acid or Lewis acid such as hydrochloric acid, sulfuric acid and ferric chloride can be suitably employed, so that it is economically advantageous as compared with the process disclosed in Patent document 6.

When 3,3,3-trifluoropropionaldehyde obtained by the second step is reacted with the oxidizing agent, a target 3,3,3-trifluoropropionic acid can be obtained (the fourth step).

Further, the present inventors found that benzyl vinyl ether represented by the formula [1] (i.e., the raw material for the hydrolysis step) can be readily produced from an industrially available starting material, more specifically from 1-halogeno-3,3,3-trifluoropropene represented by formula [4]

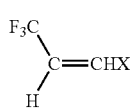

[4]

(where X is a halogen element such as fluorine, chlorine, bromine and iodine).

In other words, it is confirmed that benzyl vinyl ether represented by the formula [1] is produced with a high yield when 1-halogeno-3,3,3-trifluoropropene represented by the formula [4] is reacted in the presence of a basic substance with benzyl alcohol represented by formula [5]

$RCH_2OH$ [5]

(where R is phenyl group or a phenyl group having a substitution group represented by $R^1$, where $R^1$ is a group selected from alkyl group, alkoxy group, halogen atom and nitro group).

Further, the present inventors confirmed that benzyl alcohols ($RCH_2OH$) produced as the by-product in the hydrolysis step (or the second step) is hardly consumed by the above-mentioned side reaction thereby to remain in a reaction system (or in a tank bottom) in the stable form. The benzyl alcohols are found to be separated and collected with a high yield from a reaction solution obtained upon termination of the hydrolysis step, since they have significantly higher boiling points than the target 3,3,3-trifluoropropionaldehyde. This collection step may be referred to as "the third step". The collected benzyl alcohols can be reused for synthesis of benzyl vinyl ether at the next batch.

As discussed above, a suitable combination of the first to fourth steps allows to more advantageously produce the target 3,3,3-trifluoropropionic acid from an inexpensive starting material than in the conventional techniques.

By the way, the present applicants have already filed an application (Japanese Patent Unexamined Publication No. 2004-310880) as to a process for obtaining 3,3,3-trifluoropropionic acid, in which 1-halogeno-3,3,3-trifluoropropene represented by the formula [4] and to be used as the starting material is reacted with "cyclic secondary amines" such as piperidine to form a trifluoromethyl group-containing enamine, and then the trifluoromethyl group-containing enamine is hydrolyzed to obtain 3,3,3-trifluoropropionaldehyde, followed by oxidization of the same. Though this is also a good process, "cyclic secondary amines" which are absolutely essential for carrying out the invention are expensive and it is not easy to collect "cyclic secondary amines" from salts of "cyclic secondary amines" produced as the by-product. In contrast to this, the present invention does not require "cyclic secondary amines" and allows collecting and reusing benzyl alcohol to be used in the reaction, so that it is far more advantageous from an economical perspective.

The following scheme shows the relations among the first to fourth steps of the process according to the present invention.

SCHEME

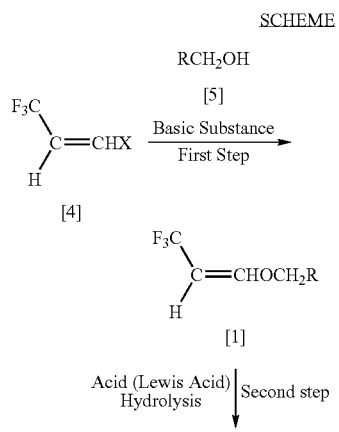

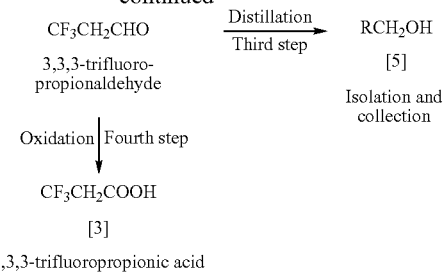

The present inventors further studied eagerly in order not to decline the quality of products during storage. With this, it was found that 3,3,3-trifluoropropionaldehyde is dramatically improved in storage stability with the addition of water, by which the above problems are solved. The step to add water may be hereinafter referred to as "step (A)". This process for improving the storage stability of 3,3,3-trifluoropropionaldehyde relates to the second aspect of the present invention.

The present inventors found not only that formation of 3,3,3-trifluoropropionaldehyde trimer represented by the formula [7], 3,3,3-trifluoropropionic acid represented by the formula [3] and others is dramatically suppressed when water is added to 3,3,3-trifluoropropionaldehyde, but also that formation of these is suppressed even in a long period of storage so as to maintain a high purity during the storage.

The second aspect of the present invention resides in producing a composition of 3,3,3-trifluoropropionaldehyde/water by adding water to 3,3,3-trifluoropropionaldehyde. With this, it was found that the composition mainly contains 3,3,3-trifluoro-1-(3,3,3-trifluoro-1-hydroxypropoxy)propan-1-ol represented by formula [6] and having a structure where 3,3,3-trifluoropropionaldehyde is hydrated and then dimerized (see the following schemes).

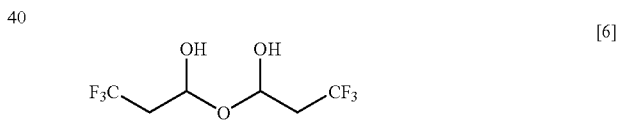

SCHEME

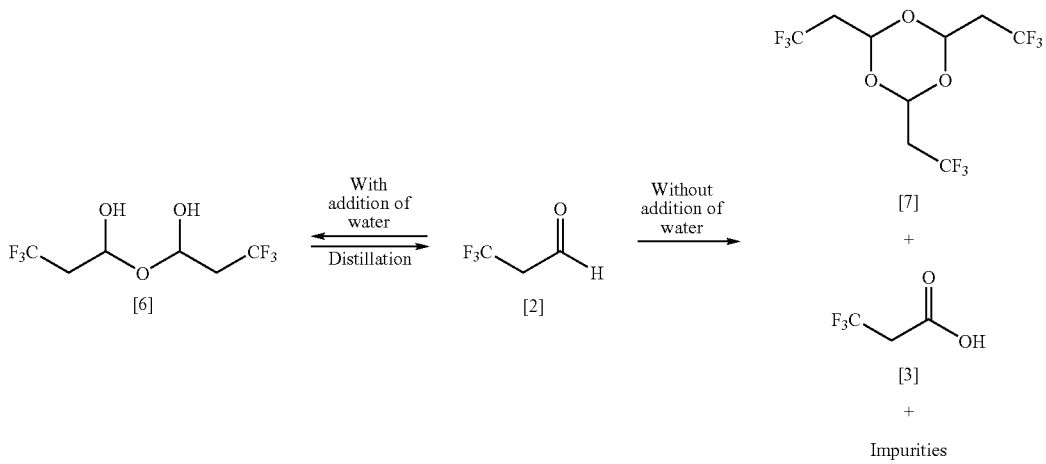

As shown in the above scheme, the present inventors found that a conversion between 3,3,3-trifluoro-1-(3,3,3-trifluoro-1-hydroxypropoxy)propan-1-ol represented by the formula [6] and 3,3,3-trifluoropropionaldehyde represented by the formula [2] is reversibly achieved. Though a large amount of 3,3,3-trifluoropropionaldehyde trimer represented by the formula [7], 3,3,3-trifluoropropionic acid represented by the formula [3] and other impurities is hitherto undesirably produced when the chemical equilibrium is caused to shift to the side of the formula [2], it is assumed to be able to dramatically suppress the formation of these.

The present inventors further found that the raw material (i.e., 3,3,3-trifluoropropionaldehyde represented by the formula [2]) can be readily collected by distilling the composition of 3,3,3-trifluoropropionaldehyde/water obtained with the addition of water.

More specifically, the second aspect of the present invention resides in including, as an essential factor, (1) "step (A)" for adding water to 3,3,3-trifluoropropionaldehyde represented by the formula [2] to produce a composition of 3,3,3-trifluoropropionaldehyde/water. The second aspect of the present invention is thus based on the step (A), but the present invention is also accomplished even when the following two steps are arbitrarily combined with the step (A):

(2) a step for storing the composition obtained in the step (A), in an air or nitrogen atmosphere (the step will be referred to as "step (B)"); and (3) a step for collecting 3,3,3-trifluoropropionaldehyde represented by the formula [2] by distilling the composition upon storage (the step will be referred to as "step (C)"). With this, 3,3,3-trifluoropropionaldehyde can be readily regenerated. This regeneration process allows retaining 3,3,3-trifluoropropionaldehyde at a high purity even after a long period of storage and allows 3,3,3-trifluoropropionaldehyde to be stored and circulated as an industrial material, and therefore it is regarded as a highly advantageous process.

DETAILED DESCRIPTION OF INVENTION

According to the first aspect of the present invention, benzyl vinyl ether represented by formula [1] and employed as a starting material is hydrolyzed by using a catalytic amount of Arrhenius acid or Lewis acid, thereby producing 3,3,3-trifluoropropionaldehyde with a yield of significantly larger than 50% (the second step). Further, it is oxidized to produce a target 3,3,3-trifluoropropionic acid with a high yield (the fourth step). Benzyl vinyl ether represented by the formula [1] can be readily produced from 1-halogeno-3,3,3-trifluoropropene represented by formula [4] and inexpensively available (the first step). Therefore, 3,3,3-trifluoropropionic acid which is an useful intermediate for medicines and agricultural chemicals while being an useful synthetic intermediate or raw material for producing functional materials such as fluorine-containing polymers can be more inexpensively produced than in conventional techniques.

According to the second aspect of the present invention, 3,3,3-trifluoropropionaldehyde serving as a compound high in usefulness as the intermediate for medicines and agricultural chemicals is dramatically improved in storage stability when water is added thereto. Additionally, 3,3,3-trifluoropropionaldehyde is readily collected by distillation, with which it is allowed to retain 3,3,3-trifluoropropionaldehyde at a high purity, and more specifically at a purity of not less than 98%, for a long period of time. This provides the effect of facilitating an industrial use of 3,3,3-trifluoropropionaldehyde.

Hereinafter, the first aspect of the present invention will be further discussed.

A functional group R included in benzyl vinyl ether used in the present invention is phenyl group or a phenyl group having a substitution group represented by $R^1$, where $R^1$ is a group selected from alkyl group, alkoxy group, halogen atom and nitro group. When $R^1$ is alkyl group or alkoxy group, it preferably has a carbon number ranging from 1 to 6, and therefore examples thereof are methyl group, ethyl group, i-propyl group, n-propyl group, n-butyl group, t-butyl group, methoxy group, ethoxy group, i-propoxy group, n-propoxy group, n-butoxy group and t-butoxy group. Further, when $R^1$ is halogen atom, it may be any of fluorine, chlorine, bromine and iodine. Further, the substitution group represented by $R^1$ may consists of a plurality of groups which are the same as or different from each other. Specific examples of R are o-tolyl group, m-tolyl group, p-tolyl group, 3,5-xylyl group, 2-ethylphenyl group, 3-ethylphenyl group, 4-ethylphenyl group, 2-chlorophenyl group, 3-chlorophenyl group and 4-chlorophenyl group, as well as phenyl group having no substitution group.

However, phenyl group having no substitution group is particularly preferable used as R since it is inexpensive and excellent in reactivity. In other words, it is particularly preferable to use benzyl(3-trifluoromethyl)vinyl ether (1-benzyloxy-3,3,3-trifluoropropene) represented by the following formula:

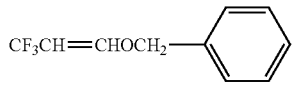

as benzyl vinyl ether represented by the formula [1].

Benzyl vinyl ether represented by the formula [1] and to be used in the reaction of the second step may be produced by any process; however, it is preferably produced from 3,3,3-trifluoropropionaldehyde employed as the starting material by the process of the first step.

Benzyl alcohol ($RCH_2OH$) formed as a by-product by the reaction of the second step is preferably separated and collected from a reaction system upon termination of the second step, by a process included in the third step.

In the specification of the present application, the first, second, third and fourth steps will be discussed hereinafter in the order mentioned.

To begin with, the first step will be discussed. The first step is to obtain benzyl vinyl ether represented by the formula [1] by reacting 1-halogeno-3,3,3-trifluoropropene represented by the formula [4] with benzyl alcohol represented by formula [5] in the presence of a basic substance.

A halogen X of 1-halogeno-3,3,3-trifluoropropene represented by the formula [4] may be any of fluorine, chlorine, bromine and iodine. Of these, 1-chloro-3,3,3-trifluoropropene to which chlorine is applied is industrially available as HCFC-1233, and therefore it is preferable to use 1-chloro-3,3,3-trifluoropropene. 1-Chloro-3,3,3-trifluoropropene includes the type of E-configuration (HCFC-1233t) and that of Z-configuration (HCFC-1233c), and these may be included singly or in combination. When the E-configuration type 1-chloro-3,3,3-trifluoropropene is used as the raw material, a main product of vinyl ether represented by the formula [1] also has the E-configuration. When the Z-configuration type one is used as the raw material, a main product of vinyl ether represented by the formula [1] also has the Z-configuration.

Benzyl alcohol represented by the formula [5] and to be used in the first step is selected according to the kind of a target of the first step, and more specifically the kind of benzyl vinyl ether represented by the formula [1]. Specific examples of benzyl alcohol are benzyl alcohol, methylbenzyl alcohol, ethylbenzyl alcohol and chlorobenzyl alcohol. Of these, benzyl alcohol having no substitution group is particularly preferable since it is the most inexpensive, readily available, and excellent in reactivity in the second step (a hydrolysis step).

The amount of benzyl alcohol used in the first step is not limited to a particular one but it is usually 1.0 to 10.0 moles, preferably 1.0 to 7.0 moles and more preferably 1.0 to 4.0 moles relative to 1.0 mole of 1-halogeno-3,3,3-trifluoropropene. Benzyl alcohol in excess of 10.0 moles is not preferable from the viewpoints of productivity and cost efficiency.

In a reaction caused at the first step, the basic substance is absolutely essential for neutralizing hydrogen halides formed by the reaction and for causing a chemical equilibrium to shift to the product side. Benzyl vinyl ether represented by the formula [1] is hardly produced without the basic substance. The kind of the basic substance is not limited to a particular one, but it is preferably an inorganic base exemplified by sodium hydroxide, sodium carbonate, sodium hydrogencarbonate, potassium hydroxide, potassium carbonate, potassium hydrogencarbonate, calcium hydroxide and lithium hydroxide. Of these bases, inexpensive sodium hydroxide and potassium hydroxide are particularly preferable. The reaction proceeds even if the basic substance is an organic base such as methylamine, dimethylamine, trimethylamine, diethylamine, triethylamine, tributylamine, pyridine, piperidine, methylpyridine, dimethylpyridine and aniline; however, the inorganic base is more preferable since the organic base is relatively expensive and burdens purification made after the reaction. The amount of the basic substance is not limited to a particular one, but it is usually 1.0 to 10.0 moles, preferably 1.0 to 6.0 moles and more preferably 1.0 to 4.0 moles relative to 1.0 mole of 1-halogeno-3,3,3-trifluoropropene. The basic substance in excess of 10.0 moles is not preferable from the viewpoints of productivity and cost efficiency, even though it has no effect on productivity. On the other hand, the basic substance less than 1.0 mole is reduced in conversion rate into benzyl vinyl ether so as to make it difficult to refine benzyl vinyl ether by isolation after termination of the reaction, and therefore it is also not preferable.

At the first step, water may be added for the purpose of increasing solubility of the basic substance in a reaction system, which is preferable in usual cases. The amount of added water is preferably within a range of from 0.01 to 2 g, more preferably within a range of from 0.1 to 1 g relative to 1 g of the basic substance.

At the first step, a phase transfer catalyst may be added for the purpose of promoting the progress of the reaction. The kind of the phase transfer catalyst is not limited to a particular one, but it is preferably crown ethers, quaternary ammonium salt, phosphonium salt or the like. Concrete examples of these are 18-crown-6-ether, tetrabutylammonium chloride, tetrabutylammonium bromide and tetrabutylphosphonium bromide. The amount of the phase transfer catalyst is not limited to a particular one but it is usually 0.01 to 30 parts by weight, preferably 0.1 to 15 parts by weight and more preferably 0.5 to 10 parts by weight relative to 100 parts by weight of 1-halogeno-3,3,3-trifluoropropene. The phase transfer catalyst having an amount of not less than 30 parts by weight is not preferable from the viewpoints of productivity and cost efficiency, even though it has no effect on reactivity. However, it will be understood from Example 1 as discussed below that the phase transfer catalyst is not always necessary in the first step. The reaction can proceed at sufficient selectivity and rate, even if the phase transfer catalyst does not exist.

The reaction temperature during the first step is usually within a range of from 0 to 200° C., preferably within a range of from 20 to 150° C. and more preferably within a range of from 30 to 100° C.

The reaction at the first step may be caused in a pressure-resistant reactor such as an autoclave, but usually caused in air at atmospheric pressure. Both 1-halogeno-3,3,3-trifluoropropene (i.e., the raw material) and benzyl vinyl ether (i.e., the target substance) are stable in air atmosphere, so that the reaction may be made in the air.

The reaction time in the first step is not limited to a particular one but it is preferable to terminate a reaction process as soon as an approach of the end of the reaction is confirmed from the progress of the reaction, for example, by using gas chromatography. With this, a reaction mixture containing vinyl ether represented by the formula [1] is obtained.

The thus obtained reaction mixture may be provided as the raw material to the second step without making a refining treatment thereon, or may be provided to the second step upon being subjected to a refinement in order to remove unreacted materials and by-products therefrom.

The way of carrying out the refining treatment is not limited to a particular one, but it is preferably one for obtaining "an organic layer in which an unreacted alcohol is mixed with vinyl ether" by separating solid substances such as precipitated inorganic salts from a reaction system where the first step has terminated and then by making a rinse and a separation into two layers. Further, the way is also preferably one for obtaining "a fraction in which an unreacted alcohol is mixed with vinyl ether" by separating solid substances such as precipitated inorganic salts from the reaction system where the first step has terminated and then by conducting a simple distillation (or a crude distillation) thereon.

In a case where "benzyl alcohol" is used as alcohol, "an acetal-producing reaction" between free alcohol and benzyl vinyl ether is suppressed in the subsequent second step (or the hydrolysis step), as discussed above. Hence, a crude refinement is enough to achieve the refining treatment after termination of the first step, and therefore it is not necessary to completely eliminate an excessive alcohol from the system.

Then, the second step will be discussed. The second step is to hydrolyze benzyl vinyl ether represented by the formula [1] in the presence of a catalyst selected from Arrhenius acid and Lewis acid thereby obtaining a target 3,3,3-trifluoropropionaldehyde.

Benzyl vinyl ether used in the second step may be any kind of compounds as far as defined by the formula [1]. Of these, 1-benzyloxy-3,3,3-trifluoropropene where R is phenyl group having no substitution group is particularly preferable.

Every benzyl vinyl ether is economically preferably produced by the above-mentioned process of the first step; however, it is not always limited to these, and those produced by other processes may be unavoidably used as a raw material for the second step.

The catalyst used in the second step (or the hydrolysis step) is at least one catalyst selected from Arrhenius acid and Lewis acid. "Arrhenius acid" is one of chemical species having a property of dissociating proton, and in general it is a substance (or an acid) having a pH of not larger than 6 when dissolved in water in a concentration of 0.1 mol·dm$^{-3}$. Of these acids, it is preferable to use those classified as "a strong acid" or "an inferior acid", such as hydrochloric acid, sulfuric acid, trifluoromethanesulfonic acid, hydrofluoric acid, hydrobromic acid, hydroiodic acid, methanesulfonic acid, benzenesulfonic acid, trifluoroacetic acid, phosphoric acid, silicic acid, boric acid, formic acid, acetic acid, propionic acid, butyric acid, valeric acid, pivalic acid, oxalic acid, succinic acid, adipic acid and crotonic acid. Of these, hydrochloric acid or sulfuric acid is particularly preferable since they are inexpensive and excellent in catalytic activity. Acids having a strong oxidizing property, such as nitric acid, perchloric acid, chloric acid, permanganic acid and chromic acid also have the function of a catalyst for hydrolysis to produce 3,3,3-trifluoropropionaldehyde, but not preferable to use since they sometimes oxidize an obtained target to produce 3,3,3-trifluoropropionic acid.

"Lewis acid" is one of chemical species including an atom having an empty orbital for accepting electron pair and is exemplified by oxides or complexes of transition metals. Specific examples of these are $Ag^+$, $I^+$, $SO_3$, $SO_2$, $BF_3$, $BCl_3$, ammonium chloride ($AlCl_3$), $AlBr_3$, iron(III) chloride ($FeCl_3$), $FeBr_3$, $Fe_2O_3$, FeO, metallocene such as ferrocene, cobaltocene and nickelocene, $Cu_2O$, CuO, copper (II) chloride ($CuCl_2$), $SbCl_5$, tin(IV) chloride ($SnCl_4$), titanium chloride ($TiCl_4$), $PdCl_2$ and $Pd(OCOCH_3)_2$. Of these acids, iron (III) chloride ($FeCl_3$) is particularly preferable since it is excellent in catalytic activity and inexpensive.

The catalyst to be is usually 0.0001 to 0.8 equivalent, preferably 0.005 to 0.5 equivalent and more preferably 0.01 to 0.3 equivalent relative to the vinyl ether represented by the formula [1]. The equivalent number is represented by a value obtained by dividing "the number of moles of the catalyst" by "a valency number of the catalyst". "A valency number" means in Arrhenius acid the number of valence that the acid has (e.g., hydrochloric acid has a valency number of 1 while sulfuric acid has a valency number of 2), while meaning in Lewis acid the number of valency of an atom having an empty orbital (e.g., $FeCl_3$ has a valency number of 3 while CuO has a valency number of 2).

The amount of water to be used in the second step or in hydrolysis (or the total amount of water as a solvent when the catalyst is used as an aqueous solution) is usually 1 to 2 moles, preferably 1 to 20 moles and more preferably 1 to 5 moles relative to 1 mole of benzyl vinyl ether. Water having an amount exceeding 20 moles is economically disadvantageous in terms of productivity and the like, while water having an amount of less than 1 mole not only slows down the target reaction but also tends to form a by-product dibenzylether to cause a collection rate reduction of benzyl alcohol, so as not to be preferable.

The reaction temperature during the second step is usually within a range of from 50 to 150° C. and preferably within a range of from 70 to 130° C. The reaction of the second step may be caused at atmospheric pressure, an applied pressure or reduced pressure, but preferably caused at atmospheric pressure since it is the readiest.

The thus obtained 3,3,3-trifluoropropionaldehyde is oxidized by oxygen contained in air when brought into contact with air in the presence of "a transition metal compound (or a catalyst formed of transition metals such as $FeCl_3$, $FeBr_3$, $Fe_2O_3$, $Cu_2O$ and Pd)" thereby sometimes producing 3,3,3-trifluoropropionic acid. However, such an aerial oxidation is not widely made. Even if the aerial oxidation is made, it is not necessary to conduct the reaction of the second step in inert gases such as nitrogen and helium since the compound obtained by the oxidation is the target of the present invention.

An embodiment of the second step is not limited to a particular one. However, it is preferable to mix the raw material (i.e., benzyl vinyl ether represented by the formula [1]) with the catalyst and water successively or continuously, with which a reaction can be readily controlled.

It is particularly preferable to cause the reaction of the second step at a temperature sufficient to distill the target 3,3,3-trifluoropropionaldehyde as a fraction (or at a temperature of at least not less than the boiling point of the compound), and then to distill the produced 3,3,3-trifluoropropionaldehyde continuously and concurrently with the progress of the reaction. According to this method, 3,3,3-trifluoropropionaldehyde can be smoothly collected concurrently with the progress of the reaction. Additionally, with this method, the equilibrium for producing 3,3,3-trifluoropropionaldehyde is caused to shift more to the target side since the target substance is constantly removed from the system, thereby obtaining 3,3,3-trifluoropropionaldehyde with a higher yield. The target 3,3,3-trifluoropropionaldehyde has a boiling point much lower than the raw material (i.e., benzyl vinyl ether represented by the formula [1]) or than benzyl alcohol represented by the formula [5], and therefore never forms an azeotropic mixture with these.

In view of the above, a particularly preferable embodiment is a process for causing the reaction of the second step at a temperature of not less than the boiling point of 3,3,3-trifluoropropionaldehyde at atmospheric pressure and then continuously or successively distilling the thus produced 3,3,3-trifluoropropionaldehyde as a fraction (see Examples 1 to 3 as will be discussed below).

As the second step or the hydrolysis proceeds, benzyl alcohol as by-product is increased in the reaction system (or in the tank bottom), which never causes a yield reduction of 3,3,3-trifluoropropionaldehyde since "acetal" is difficult to be produced between benzyl alcohol and the unreacted benzyl vinyl ether as discussed above, even if benzyl alcohol is increased. However, the process may be one in which the reaction of the second step is conducted under a reflux condition and thereafter 3,3,3-trifluoropropionaldehyde is distilled and collected after termination of the reaction (Example 4).

The reaction time is not limited to a particular one. It is preferable to terminate a reaction process as soon as an approach of the end is confirmed from the progress of the reaction, for example, by using gas chromatography.

Then, the third step will be discussed. The third step is to distill off 3,3,3-trifluoropropionaldehyde produced in the second step as a fraction and to collect benzyl alcohol produced as the by-product by a further distillation.

Benzyl alcohol can be collected upon collecting 3,3,3-trifluoropropion-aldehyde by distillation, by heating at least to a temperature where benzyl alcohol is distilled (or at least to the boiling point of benzyl alcohol, i.e., 203 to 205° C.) at atmospheric pressure, or by heating to a temperature meeting a reduced pressure. Benzyl alcohol is hard to produce "acetal" in the reaction system of hydrolysis (or in the presence of water) as discussed above, so as to be collected with an excellently high yield as will be discussed below in Examples 1 and 2.

Then, the fourth step will be discussed. The fourth step is to oxidize 3,3,3-trifluoropropionaldehyde produced in the second step with an oxidizing agent to obtain 3,3,3-trifluoropropionic acid.

In the fourth step, the reaction mixture obtained in the second step may be used as it is as the raw material; however, it is preferable, in order to obtain a good reactivity, to isolate 3,3,3-trifluoropropionaldehyde or to separate excess bases and by-product salts and then to provide it as the raw material.

The oxidizing agent used in the fourth step is preferably peroxide-based one exemplified by potassium permanganate, potassium chromate, potassium bichromate, peracetic acid, trifluoroperacetic acid, sodium chlorate, sodium bromate, sodium iodate, and a persulfuric acid-based oxidizing agent such as the above-mentioned Oxone (registered trade name) (2 $KHSO_5.K_2SO_4.KHSO_4$).

The present inventors found that nitric acid is particularly preferably used in the fourth step. Nitric acid is a reagent inexpensive as compared with the above-mentioned peroxides and is readily handled even in a massive scale. Therefore, it is particularly preferable to use nitric acid in the fourth step of the present invention as the oxidizing agent.

Nitric acid to be used usually has a concentration of not less than 30%. However, in view of productivity and cost efficiency, nitric acid preferably has a concentration of 50 to 90%, and more preferably 60 to 70%.

The amount of nitric acid to be used is usually not less than 1 mole, preferably 1 to 5 moles, and more preferably 1 to 2 moles relative to 1 mole of 3,3,3-trifluoropropionaldehyde. Nitric acid having an amount exceeding 5 moles is not preferable in view of productivity and cost efficiency.

The reaction temperature is usually within a range of from −10 to 100° C., preferably within a range of from −5 to 70° C., and more preferably within a range of from 0 to 50° C.

In a case where nitric acid is used as the oxidizing agent, nitrite preferably coexists therewith for the purpose of carrying out the oxidation reaction more smoothly. Nitrite to be used usually has an amount of 0.5 to 20 mol %, preferably has an amount of 1 to 15 mol %, and more preferably has an amount of 2 to 10 mol % based on 1 mole of nitric acid. Sodium nitrite, potassium nitrite or the like is preferably used as nitrite.

In the fourth step, a reaction is caused in air at atmospheric pressure. The reaction time is not limited to a particular one and it is preferable to terminate a reaction process as soon as an approach of the end is confirmed from the progress of the reaction, for example, by using gas chromatography.

An embodiment of the reaction of the fourth step is not limited to a particular one. However, it is preferable to successively or continuously mix the raw material (i.e., 3,3,3-trifluoropropionaldehyde) with the oxidizing agent, with which the reaction can be readily controlled.

A treatment made after the reaction is not limited to a particular one. A reaction solution is brought into contact with an organic solvent to extract a target substance therefrom into an organic phase and then is subjected to a usual process such as distillation, thereby obtaining 3,3,3-trifluoropropionic acid.

Hereinafter, the second aspect of the present invention will be discussed in detail. In the specification of the present application, a step (A), a step (B) and a step (C) will be discussed in the order mentioned.

To begin with, a step A will be discussed. The raw material for the reaction of the present invention (i.e., 3,3,3-trifluoropropionaldehyde represented by the formula [2]) can be obtained by conventional techniques disclosed in the above-mentioned Patent documents and Non-patent documents.

The amount of water added in the present invention is usually 0.1 to 80 g, preferably 2 to 50 g, more preferably 3 to 20 g relative to 100 g of 3,3,3-trifluoropropionaldehyde. The amount of added water of less than 0.1 g does not provide a sufficient stabilization effect, so as not to be preferable. The amount of added water of not less than 80 g may provide an equal stabilization effect, but it is not preferable from the viewpoint not only of a collection yield reduction of 3,3,3-trifluoropropionaldehyde at the time of collection but also of productivity. In an actual reaction, a method of weighing a suitable amount of 3,3,3-trifluoropropionaldehyde and water and then mixing these is employed in order to add a required and sufficient amount of water.

Even if 3,3,3-trifluoropropionaldehyde used in this step itself contains water, a sufficient stabilization effect cannot be obtained when the water content is less than 0.1 g relative to 100 g of 3,3,3-trifluoropropionaldehyde, as will be discussed in Comparative Examples 1 to 2. Therefore, it is preferable to provide the above-mentioned amount of water by adding an extra water, in order to obtain the sufficient stabilization effect.

The temperature at the time of addition of water is usually within a range of from −30 to 55° C., preferably within a range of from −30 to 50° C. It is preferable not to exceed 55° C. since 3,3,3-trifluoropropionaldehyde has a low boiling point (i.e., a boiling point of 55° C.). 3,3,3-Trifluoropropionaldehyde may be mixed with water concurrently, but it is preferable to previously charge one of 3,3,3-trifluoropropionaldehyde and water into a reactor and then to successively or continuously charge the other thereinto, with which an increase of reaction temperature is readily suppressed.

In the present invention, 3,3,3-trifluoropropionaldehyde and water weighed to have a suitable amount are mixed in a reactor, followed by storage in an air or nitrogen atmosphere. Additionally, the reactor to which water is added is not limited to a particular one, and therefore suitably selected by the person skilled in the art.

Then, a step B will be discussed. Concerning storage made after the addition of water according to the present invention, the temperature during it is usually −50 to 90° C., preferably −30 to 60° C. and more preferably −30 to 30° C.

The pressure applied during the storage is not limited to a particular one. Therefore, the storage may be made at atmospheric pressure upon introducing air, nitrogen or inert gases such as argon, or made under a closed and pressurized condition. 3,3,3-Trifluoropropionaldehyde provided as the raw material has a low boiling point, and therefore it is important in performing this step to bring these into a liquid or solid state. To accomplish this, the temperature and pressure are suitably selected.

The storage can be carried out in an air or inert gaseous atmosphere at atmospheric pressure when at room temperature or lower, which is preferable from its easiness. It is one preferable embodiment to perform the storage in the presence of air at atmospheric pressure at a temperature within a range of from −10 to 25° C., as discussed in Examples 6 to 11.

In a contrary case where the storage is carried out at a temperature of not lower than the boiling point of 3,3,3-trifluoropropionaldehyde (i.e., not lower than 55° C.), 3,3,3-trifluoropropionaldehyde is sometimes vaporized. In this case, the reaction is caused preferably under a closed and pressurized condition upon bringing the interior of a pressure-resistant reactor to an inert gaseous atmosphere, in order to keep 3,3,3-trifluoropropionaldehyde (provided as the raw material) in a liquid state. It is to be noted that there is little merit in storing at a temperature of not less than 55° C.

Then, a step C will be discussed. In the present invention, 3,3,3-trifluoropropionaldehyde and water weighed to have a suitable amount are mixed in a reactor and then stored. Thereafter, distillation is conducted on a mixture, thereby readily collecting 3,3,3-trifluoropropionaldehyde.

An apparatus for distillation is not limited to a particular one and therefore suitably selected by the person skilled in the art. The temperature and pressure (e.g., a condition of atmospheric pressure or of reduced pressure) are also suitably selected by the person skilled in the art. In this step, heating may reach a temperature at which 3,3,3-trifluoropropionaldehyde is distilled under atmospheric pressure (3,3,3-trifluoropropionaldehyde has a boiling point of 55° C.) or higher, or may reach a temperature meeting a reduced pressure. However, it is preferable to heat at atmospheric pressure in view of the low boiling point of 3,3,3-trifluoropropionaldehyde and in view of easiness of the operation.

For example, it will be understood from Examples 9 to 11 to be one preferable embodiment to distill 3,3,3-trifluoropropionaldehyde at a temperature of not less than its boiling point, from the viewpoint of being capable of efficiently collecting the target substance alone from the reaction system containing water.

In the second aspect of the present invention, formation of 3,3,3-trifluoropropionaldehyde trimer represented by a formula [7], 3,3,3-trifluoropropionic acid represented by the formula [3] and impurities is significantly suppressed as compared with the following Comparative Examples, which allows a long period of storage (for example, 7 days in Examples 6 to 11).

Further, the mixture is distilled at atmospheric pressure in Examples 9 11, thereby obtaining 3,3,3-trifluoropropionaldehyde with a high collection yield.

The second aspect of the present invention resides in obtaining a composition of 3,3,3-trifluoropropionaldehyde/water by adding water to 3,3,3-trifluoropropionaldehyde thereby producing 3,3,3-trifluoro-1-(3,3,3-trifluoro-1-hydroxypropoxy)propan-1-ol (represented by formula [6] and having a structure where 3,3,3-trifluoropropionaldehyde itself is hydrated and then dimerized). This compound is white solid in room temperature, and is so highly stable as not to be changed even after stored at room temperature for a long period of time. In the present invention, when this compound is produced in a part of the reaction system, or when 3,3,3-trifluoro-1-(3,3,3-trifluoro-1-hydroxypropoxy)propan-1-ol in which all 3,3,3-trifluoropropionaldehyde are represented by the formula [6] is produced, formation of 3,3,3-trifluoropropionaldehyde trimer represented by the formula [7], 3,3,3-trifluoropropionic acid represented by the formula [3] and impurities is dramatically suppressed.

3,3,3-trifluoro-1-(3,3,3-trifluoro-1-hydroxypropoxy)propan-1-ol represented by the formula [6] itself may be a crystal without a solvent or may be dissolved in water to be in the form of an aqueous solution. Additionally, a compound containing 3,3,3-trifluoro-1-(3,3,3-trifluoro-1-hydroxypropoxy)propan-1-ol represented by the formula [6] in its reaction system is distilled after being stored, thereby allowing readily collecting 3,3,3-trifluoropropionaldehyde.

As will be discussed in Examples 9 to 11, it is one preferable embodiment to readily collect 3,3,3-trifluoropropionaldehyde with a high yield by adding water to produce the composition of 3,3,3-trifluoropropionaldehyde/water (in the step A), by storing it in the presence of air (in the step B), and then by conducting distillation after the storage (at a boiling point of 55° C.).

As discussed above, the above steps are combined so as to allow collecting the target substance (i.e., 3,3,3-trifluoropropionaldehyde represented by the formula [2]) with a high purity.

EXAMPLES

Hereinafter, the present invention will be specifically discussed with reference to Examples; however, the present invention is not limited to these Examples. Here, "%" used for a composition analysis value is by area of a composition, obtained by directly measuring a product by gas chromatography. Additionally, water content percentages are by weight, obtained by measuring by a Karl Fischer's moisture meter.

Examples 1 to 5 illustrate the first aspect of the present invention. Examples 6 to 11 illustrate the second aspect of the present invention. Comparative Examples 1 and 2 are as opposed to Examples 6 to 11.

Example 1

(First Step, Second Step and Third Step)

(First Step) A 100 mL stainless steel autoclave cooled with dry ice and acetone was previously charged with: a solution obtained by dissolving 19 g (0.34 mole) of KOH in 37.2 g (0.34 mole) of benzyl alcohol and 6.2 g of water; and 22.5 g (0.17 mole) of (1Z)-1-chloro-3,3,3-trifluoropropene. It was heated to about 22° C. and then stirred for 1 hour. Then, it was heated with stirring at 70° C. for 12 hours. A reaction solution was found by measurement with gas chromatography to have a composition of: 49.5% of benzyl alcohol; 0.5% of (1Z)-1-chloro-3,3,3-trifluoropropene (raw material); 45.0% of (1Z)-1-benzyloxy-3,3,3-trifluoropropene; and 5.0% of (1E)-1-benzyloxy-3,3,3-trifluoropropene.

Upon filtering precipitated salts off, flash distillation was made to collect a fraction of 90-110° C./2.7 MPa thereby obtaining 54 g of a mixture. The mixture was measured by gas chromatography, thereby being found to have a composition of: 49.7% of benzyl alcohol; 45.3% of (1Z)-1-benzyloxy-3,3,3-trifluoropropene; and 5.0% of (1E)-1-benzyloxy-3,3,3-trifluoropropene.

(Second Step) 54 g of the thus obtained mixture, 1.3 g (0.07 mole) of water and 2.7 g (0.026 mole) of 35% hydrochloric acid were charged into a 100 mL glass three-neck flask equipped with a magnetic stirrer, a thermometer, a distillation column, a cooling tube and a receiver flask, and then heated and stirred at a reaction temperature of from 100 to 120° C. A fraction distilled out of the mixture at boiling points of 55 to 57° C. was collected, thereby obtaining a target 3,3,3-trifluoropropionaldehyde (Yield: 13.8 g, Percentage yield only in the second step: 91.7%, Total yield in the first and second steps: 71.7%, Purity: 99%).

(Third Step) Distillation was further continued even after the distillation of 3,3,3-trifluoropropionaldehyde was terminated, thereby collecting benzyl alcohol (Collected amount: 26 g, Collection yield: 70%).

[Property Data]

(1Z)-1-benzyloxy-3,3,3-trifluoropropene:
$^1$H-NMR spectrum (400 MHz, CDCl$_3$) δ (ppm): 4.67 (1H, m), 4.98 (2H, s), 6.38 (1H, d, J=6.8 Hz), 7.35 (5H, m);
$^{19}$F-NMR spectrum (400 MHz, CDCl$_3$, CFCl$_3$) δ (ppm): −57.92 (3F, d, J=6.3 Hz).

(1E)-1-benzyloxy-3,3,3-trifluoropropene:
$^1$H-NMR spectrum (400 MHz, CDCl$_3$) δ (ppm): 4.81 (2H, s), 5.06 (1H, dq, J=12.6, 6.3 Hz), 7.12 (1H, dq, J=12.6, 2.0 Hz), 7.35 (5H, m);
$^{19}$F-NMR spectrum (400 MHz, CDCl$_3$, CFCl$_3$) δ (ppm): −59.81 (3F, d, J=6.3 Hz).

3,3,3-Trifluoropropionaldehyde:
$^1$H-NMR spectrum (400 MHz, CDCl$_3$) δ (ppm): 3.62 (3H, s), 4.92 (1H, dq, J=13.2, 6.4 Hz), 7.08 (1H, dq, J=13.2, 2.0 Hz);
$^{19}$F-NMR spectrum (400 MHz, CDCl$_3$, CFCl$_3$) δ (ppm): −59.59 (3F, d, J=6.4 Hz).

Example 2

(First Step, Second Step and Third Step)

(First Step) A 100 mL stainless steel autoclave cooled with dry ice and acetone was previously charged with: a solution obtained by dissolving 19 g (0.34 mole) of KOH in 37.2 g (0.34 mole) of benzyl alcohol and 6.2 g of water; 22.5 g (0.17 mole) of (1Z)-1-chloro-3,3,3-trifluoropropene; and 0.56 g of 18-crown-6-ether. It was heated to about 22° C. and then stirred for 1 hour. Then, it was heated with stirring at 70° C. for 12 hours. A reaction solution was found by measurement with gas chromatography to have a composition of: 50% of benzyl alcohol; 44.8% of (1Z)-1-benzyloxy-3,3,3-trifluoropropene; and 5.2% of (1E)-1-benzyloxy-3,3,3-trifluoropropene.

Upon filtering precipitated salts off, flash distillation was made to collect a fraction of 90-110° C./2.7 MPa thereby obtaining 53.5 g of a mixture. The mixture was measured by gas chromatography, thereby being found to have a composition of: 49.9% of benzyl alcohol; 44.9% of (1z)-1-benzyloxy-3,3,3-trifluoropropene; and 5.2% of (1E)-1-benzyloxy-3,3,3-trifluoropropene.

(Second Step) 53.5 g of the thus obtained mixture, 6.2 g (0.34 mole) of water and 1.4 g (0.0086 mole) of $FeCl_3$ were charged into a 100 mL glass three-neck flask equipped with a magnetic stirrer, a thermometer, a distillation column, a cooling tube and a receiver flask, and then heated and stirred at a reaction temperature of from 100 to 120° C. A fraction distilled out of the mixture at boiling points of 55 to 57° C. was collected, thereby obtaining a target 3,3,3-trifluoropropionaldehyde (Collected amount: 12 g, Collection yield only in the second step: 80.8%, Total collection yield in the first and second steps: 62.4%, Purity: 99%).

(Third Step) Distillation was further continued even after the distillation of 3,3,3-trifluoropropionaldehyde was terminated, thereby collecting benzyl alcohol (Collected amount: 31 g, Collection yield: 83%).

Example 3

(First Step and Second Step)

(First Step) A 1000 mL stainless steel autoclave cooled with dry ice and acetone was previously charged with: a solution obtained by dissolving 323 g (5.77 mole) of KOH in 415 g (3.84 mole) of benzyl alcohol and 138 g of water; 500 g (3.83 mole) of (1E)-1-chloro-3,3,3-trifluoropropene; and 12.5 g of tetrabutylammonium bromide. It was heated to about 22° C. and then stirred for 1 hour. Then, it was heated with stirring at 80° C. for 24 hours. A reaction solution was found by measurement with gas chromatography to have a composition of: 3.2% of benzyl alcohol; 4.2% of (1E)-1-chloro-3,3,3-trifluoropropene (the raw material); 86.3% of (1E)-1-benzyloxy-3,3,3-trifluoropropene; 4.4% of (1Z)-1-benzyloxy-3,3,3-trifluoropropene; and 1.3% of 1,1,1-trifluoro-3,3-dibenzyloxypropane.

Upon filtering precipitated salts off, flash distillation was made to collect a fraction of 81-85° C./2 kPa thereby obtaining 643 g of a mixture. The mixture was measured by gas chromatography, thereby being found to have a composition of: 2.5% of benzyl alcohol; 92.4% of (1E)-1-benzyloxy-3,3,3-trifluoropropene; 4.6% of (1Z)-1-benzyloxy-3,3,3-trifluoropropene; and 0.1% of 1,1,1-trifluoro-3,3-dibenzyloxypropane.

(Second Step) 643 g of the thus obtained mixture, 69 g (3.83 mole) of water and 15.5 g (0.155 mole) of 98% sulfuric acid were charged into a 1000 mL glass three-neck flask equipped with a magnetic stirrer, a thermometer, a distillation column, a cooling tube and a receiver flask, and then heated and stirred at a reaction temperature of from 100 to 120° C. A fraction distilled out of the mixture at boiling points of 55 to 57° C. was collected, thereby obtaining target 3,3,3-trifluoropropionaldehyde (Collected amount: 300 g, Collection yield only in the second step: 86.8%, Total collection yield in the first and second steps: 70%, Purity: 99%).

In Examples 1 to 3 as discussed above, the second step (or hydrolysis) is carried out by a process for successively distilling out the product (i.e., 3,3,3-trifluoropropionaldehyde) as fractions. The yield of the target substance collected by isolation, only in the second step, reached 80.8 to 91.7%. Additionally, collection of benzyl alcohol was performed after termination of the reaction of Examples 1 and 2, with which it is found that benzyl alcohol can be collected with a yield in excess of 80%.

Example 4

(Second Step)

34 g of a mixture obtained by the same process as Example 3 (the mixture having a composition of: 2.5% of benzyl alcohol; 92.7% of (1E)-1-benzyloxy-3,3,3-trifluoropropene; 4.7% of (1Z)-1-benzyloxy-3,3,3-trifluoropropene; and 0.1% of 1,1,1-trifluoro-3,3-dibenzyloxypropane), 1.5 g (0.08 mole) of water and 0.67 g (0.007 mole) of 98% sulfuric acid were charged into a 100 mL glass three-neck flask equipped with a magnetic stirrer, a thermometer and a reflux cooling tube, and then heated and stirred at a reaction temperature of 100° C. for 2 hours. It was found by measurement with gas chromatography that a reaction solution had a composition of: 66.2% of a target 3,3,3-trifluoropropionaldehyde; 1% of (1E)-1-benzyloxy-3,3,3-trifluoropropene; 0.4% of (1Z)-1-benzyloxy-3,3,3-trifluoropropene; 1.4% of 1,1,1-trifluoro-3,3-dibenzyloxypropane; 16% of benzyl alcohol; 3.8% of dibenzyl ether; and 11.2% of others. Upon replacing the reflux cooling tube with a distillation column and a receiver flask, a fraction distilled out of the mixture at boiling points of 55 to 57° C. was collected, thereby obtaining a target 3,3,3-trifluoropropionaldehyde (Collected amount: 10 g, Collection yield: 53.9%, Purity: 99%).

In Example 4 as discussed above, the second step (hydrolysis) was carried out under a reflux condition and additionally distillation of 3,3,3-trifluoropropionaldehyde by isolation was made after termination of the reaction. The yield in the second step reached about 54%, though slightly less than that in the process of Examples 1 to 3. It is found from this that 3,3,3-trifluoropropionaldehyde can be produced as a main component also in this process.

Example 5

(Fourth Step)

In an ice bath, a 50 mL glass flask including a magnetic stirrer and an opened cooling tube was charged with 14.1 g (0.13 mole) (1.44 equivalents) of 60% sulfuric acid and 0.1 g (8.9 mole) (10 mol %) of sodium nitrite, to which 10 g (0.09 mole) (1.0 equivalent) of 3,3,3-trifluoropropionaldehyde obtained in Example 4 was added dropwise over 1 hour with stirring. After stirring for 1 hour while cooling with ice, it was further stirred for 2 hours at room temperature. Upon the addition of 20 g of purified water to a reaction mixture solution, an organic substance was extracted with 40 ml of diisopropyl ether two times by using a separating funnel. An organic layer was dried with magnesium sulfate, from which a solvent was distilled off (40° C., 6.66 kPa), followed by distillation at atmospheric pressure (boiling point or column top temperature: 136° C.), thereby obtaining the target 3,3,3-trifluoropropionic acid Collected amount: 6.9 g, Collection yield: 61%, Purity: 94%).

[Storage Stability of 3,3,3-Trifluoropropionaldehyde in Examples 6 to 8]

Three kinds of samples each of which contained 5 wt % water were prepared by adding water to 3,3,3-trifluoropropionaldehyde. Immediately after the addition of water (10 minutes after the addition of water in actuality), 3,3,3-trifluoropropionaldehyde was analyzed by $^1$H-NMR spectrum, $^{19}$F-NMR spectrum, $^{13}$C-NMR, mass spectrum and IR analysis, thereby confirming that 3,3,3-trifluoro-1-(3,3,3-trifluoro-1-hydroxypropoxy)propan-1-ol represented by formula [2] was produced (Conversion rate: 100%).

$^1$H-NMR (Standard substance: TMS, Solvent: DMSO-d6) δ (ppm): 2.49 (4H, m), 5.20 (2H, dt, J=8.0 Hz, 5.5 Hz), 6.63 (2H, d, J=8.0 Hz)

$^{19}$F-NMR (Standard substance: CFCl$_3$, Solvent: acetone-d6) δ (ppm): −62.70 (6F, t, J=11 Hz)

$^{13}$C-NMR (Standard substance: solvent, Solvent: acetone-d6) δ (ppm): 41.84 (q, J=27 Hz), 88.16 (q, J=4.4 Hz), 126.49 (q, J=275 Hz)

Mass spectrum:

TABLE 1

| Obsd m/z | Assignment | Ionization method |
|---|---|---|
| 83 | $CF_3CH_2^+$ | EI |
| 113 | $CF_3CH_2CHOH^+$ | |
| 129 | $CF_3CH_2CH(OH)O^+$ | |
| 159 | $CF_3CH_2CH(OH)OCHOH^+$ | |
| 242 | $C_6H_8F_6O_3^+$ | CI |

IR: 3313, 3224 cm$^{-1}$, 1736 cm$^{-1}$ (weak)

Further, one of the samples was stored at −10° C. and another one was stored at 25° C., each of which was analyzed by gas chromatography (GC) at 1 day later, 3 days later and 7 days later, thereby obtaining results as shown in the following Table 2.

TABLE 2

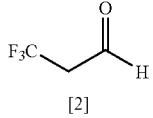

| Examples | Storage condition | | | GC composition (%) | Storage duration | | | | Main component observed by gas chromatography |
|---|---|---|---|---|---|---|---|---|---|
| | Addition amount of water (H$_2$O) | Temperature | Main component in reaction system | | 10 Minutes later | 1 Day later | 3 Days later | 7 Days later | |
| 6 | 5 wt % (based on [2]) | −10° C. |  [6] | ①②③ ④⑤ | 99.5 0 0.2 0.06 0 | 99.4 0 0.2 0.1 0 | 99.3 0 0.2 0.3 0 | 99.3 0 0.2 0.3 0 | 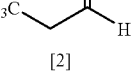 [2] |
| 7 | 5 wt % (based on [2]) | −10° C. | 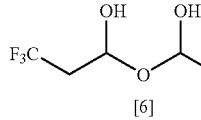 [6] | ①②③ ④⑤ | 99.6 0 0.2 0.07 0 | 99.5 0 0.2 0.1 0 | 99.4 0 0.2 0.3 0 | 99.4 0 0.2 0.3 0 |  [2] |
| 8 | 5 wt % (based on [2]) | 25° C. | 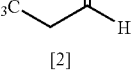 [6] | ①②③ ④⑤ | 99.6 0 0.2 0.07 0 | 99.4 0 0.2 0.2 0 | 99.1 0 0.2 0.5 0 | 99.3 0 0.3 1.2 0 | 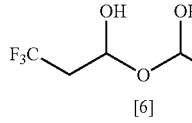 [2] |

Note:

① 3,3,3-Trifluoropropionaldehyde

② 3,3,3-Trifluoro-1-(3,3,3-trifluoro-1-hydroxypropoxy)propan-1-ol

[6]

③ Retention time at GC: 7.3 min. & 7.8 min. (Trimer)

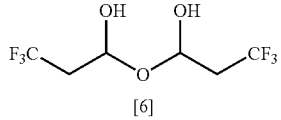

[7]

④ 3,3,3-Trifluoropropionic acid

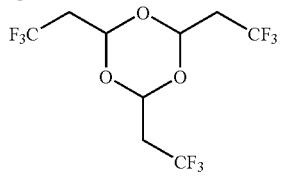

TABLE 2-continued

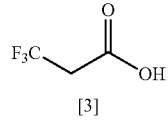
With addition of water ...

| | Storage condition | | | | Storage duration | | | | |
|---|---|---|---|---|---|---|---|---|---|
| Examples | Addition amount of water (H$_2$O) | Temperature | Main component in reaction system | GC composition (%) | 10 Minutes later | 1 Day later | 3 Days later | 7 Days later | Main component observed by gas chromatography |

[Structure: F$_3$C-CH$_2$-C(=O)-OH]  [3]

⑤Retention time at GC: 10.3 min. & 10.4 min. (Impurities)
Apparatus: SHIMADZU GC-2010
Column: DB-5 30 m 0.53 mm Film thickness of 1.5 μm
Temperature in column: 70° C. (5 min.) 20° C./min. 270° C. (5.5 min.)
Temperature at injection: 220° C.
Carrier gas: He linear velocity of 20 s
Split ratio: 1/25
Detector: FID 240° C.

3,3,3-trifluoro-1-(3,3,3-trifluoro-1-hydroxypropoxy)propan-1-ol obtained immediately after the actual addition of water and represented by formula [6] was subjected to heat (within a range of from 70 to 270° C.) resulting from a gas chromatography apparatus, when charged into the apparatus. With this, 3,3,3-trifluoro-1-(3,3,3-trifluoro-1-hydroxypropoxy)propan-1-ol obtained by the addition of water and represented by the formula [6] was completely converted into 3,3,3-trifluoropropionaldehyde represented by formula [2] as shown in Table 2, and therefore detected as 3,3,3-trifluoropropionaldehyde by gas chromatography.

It is found from Table 2 not only that formation of 3,3,3-trifluoropropionaldehyde trimer represented by the formula [7], 3,3,3-trifluoropropionic acid represented by the formula [3] and impurities is dramatically suppressed as compared with the following Comparative Examples but also that a long period of storage is allowed while keeping a high purity, more specifically a purity of not less than 98% in any of Examples 6 to 8.

Comparative Examples 1 and 2

A procedure of Examples 6 to 8 (e.g., a temperature condition and the number of days) was repeated with the exception that water was not added to 3,3,3-trifluoropropionaldehyde. Two kinds of samples were prepared and each of which was analyzed at 10 minutes later, 1 day later, 3 days later and 7 days later by gas chromatography, thereby obtaining results as shown in Table 3.

TABLE 3

F$_3$C-CH$_2$-CHO [2] — With addition of water ...

| | Storage condition | | | | Storage duration (h) | | | |
|---|---|---|---|---|---|---|---|---|
| Comparative Examples | Amount of water inherently contained in formula [2] | Temperature | | GC composition (%) | 10 Minutes later | 1 Day later | 3 Days later | 7 Days later |
| 1 | 0.04 wt % | −10° C. | | ①②③④⑤ | 99.6 / 0 / 0.2 / 0.07 / 0 | 91.7 / 0 / 5 / 0.07 / 3 | 82.2 / 0 / 11.9 / 0.1 / 5.3 | 70.9 / 0 / 13.6 / 0.3 / 14.6 |

TABLE 3-continued

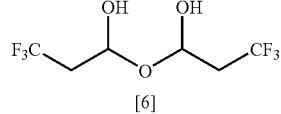

[2]

| | Storage condition | | | Storage duration (h) | | | |
|---|---|---|---|---|---|---|---|
| Comparative Examples | Amount of water inherently contained in formula [2] | Temperature | GC composition (%) | 10 Minutes later | 1 Day later | 3 Days later | 7 Days later |
| 2 | 0.04 wt % | 25° C. | ①②③④⑤ | 99.6<br>0<br>0.2<br>0.07<br>0 | 99.1<br>0<br>5.3<br>0.3<br>3 | 82.2<br>0<br>12.4<br>0.8<br>4.4 | 72.5<br>0<br>15.8<br>5.7<br>5.7 |

Note:
① 3,3,3-Trifluoropropionaldehyde
② 3,3,3-Trifluoro-1-(3,3,3-trifluoro-1-hydroxypropoxy)propan-1-ol

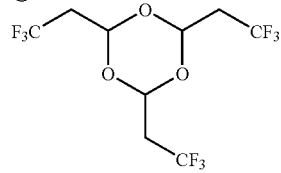

[6]

③ Retention time at GC: 7.3 min. & 7.8 min. (Trimer)

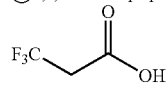

[7]

④ 3,3,3-Trifluoropropionic acid $F_3C\diagdown\diagup C(=O)OH$

[3]

⑤ Retention time at GC: 10.3 min. & 10.4 min. (Impurities)

As shown in Table 3, 3,3,3-trifluoropropionaldehyde represented by the formula [2] is gradually reduced in purity in a case where water is not added, in contrast to Examples 6 to 8. Additionally, it is found that formation of 3,3,3-trifluoropropionaldehyde trimer represented by a formula [7], 3,3,3-trifluoropropionic acid represented by the formula [3] and impurities is increased.

Even if 3,3,3-trifluoropropionaldehyde represented by the formula [2] itself contains water, a sufficient stabilization effect cannot be obtained when the water content is less than 0.1 g relative to 100 g of 3,3,3-trifluoropropionaldehyde represented by the formula [2].

Example 9

Regeneration of 3,3,3-trifluoropropionaldehyde

A 100 mL sample bottle formed of glass was charged with 40.0 g (0.357 mole and a purity of 99.5%) of 3,3,3-trifluoropropionaldehyde and 6.43 g (0.357 mole) of water and then shaken well, followed by storage in a refrigerator (5° C.). A white solid obtained at 7 days later was analyzed by $^1$H-NMR spectrum, $^{19}$F-NMR spectrum, $^{13}$C-NMR, mass spectrum and IR analysis, thereby being found to be 3,3,3-trifluoro-1-(3,3,3-trifluoro-1-hydroxypropoxy)propan-1-ol represented by the formula [6] (Purity: 99.5%, Collected amount: 43.2 g, Collection yield: 98%).

The thus obtained 3,3,3-trifluoro-1-(3,3,3-trifluoro-1-hydroxypropoxy)-Propan-1-ol was then moved to a distillation apparatus to be distilled at atmospheric pressure (boiling point: 55° C.), thereby collecting 37.2 g of 3,3,3-trifluoropropion-aldehyde with a purity of 99.5%, a yield (of 3,3,3-trifluoro-1-(3,3,3-trifluoro-1-hydroxypropoxy)propan-1-ol) of 95%, and a total yield (or a yield of trifluoro-propionaldehyde) of 93%.

Example 10

Regeneration of 3,3,3-trifluoropropionaldehyde

A 100 mL sample bottle formed of glass was charged with 40.0 g (0.357 mole and a purity of 99.5%) of 3,3,3-trifluoropropionaldehyde and 20.0 g (1.11 mole) of water and then shaken well, followed by storage in a refrigerator (5° C.). A white solid obtained at 7 days later was analyzed by $^1$H-NMR spectrum, $^{19}$F-NMR spectrum, $^{13}$C-NMR, mass spectrum and IR analysis, thereby being found to be 3,3,3-trifluoro-1-(3,3,3-trifluoro-1-hydroxypropoxy)propan-1-ol represented by the formula [6] (Purity: 99.5%, Collected amount: 43.2 g, Collection yield: 98%).

The thus obtained 3,3,3-trifluoro-1-(3,3,3-trifluoro-1-hydroxypropoxy)-propan-1-ol was then moved to a distillation apparatus to be distilled at at atmospheric pressure (boiling point: 55° C.), thereby collecting 35.6 g of 3,3,3-trifluoropropionaldehyde with a purity of 99.5%, a yield (of 3,3,3-trifluoro-1-(3,3,3-trifluoro-1-hydroxypropoxy)propan-1-ol) of 91%, and a total yield (or a yield of trifluoropropionaldehyde) of 89%.

Example 11

Regeneration of 3,3,3-trifluoropropionaldehyde

A 100 mL sample bottle formed of glass was charged with 40.0 g (0.357 mole and a purity of 99.5%) of 3,3,3-trifluoropropionaldehyde and 32.1 g (1.78 mole) of water and then shaken well, followed by storage in a refrigerator (5° C.). A white solid obtained at 7 days later was analyzed by $^1$H-NMR spectrum, $^{19}$F-NMR spectrum, $^{13}$C-NMR, mass spectrum and IR analysis, thereby being found to be 3,3,3-trifluoro-1-(3,3,3-trifluoro-1-hydroxypropoxy)propan-1-ol represented by the formula [6] (Purity: 99.5%, Collected amount: 43.2 g, Collection yield: 98%).

The thus obtained 3,3,3-trifluoro-1-(3,3,3-trifluoro-1-hydroxypropoxy)-propan-1-ol was then moved to a distillation apparatus to be distilled at atmospheric pressure (boiling point: 55° C.), thereby collecting 34.8 g of 3,3,3-trifluoropropionaldehyde with a purity of 99.5%, a yield (of 3,3,3-trifluoro-1-(3,3,3-trifluoro-1-hydroxypropoxy)propan-1-ol) of 89%, and a total yield (or a yield of trifluoropropionaldehyde) of 87%.

What is claimed is:

1. A process for producing 3,3,3-trifluoropropionic acid represented by formula [3]

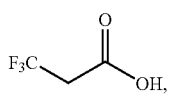

[3]

comprising the steps of:
hydrolyzing benzyl vinyl ether represented by formula [1]

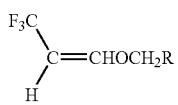

[1]

where R is one of a phenyl group and a phenyl group having a substitution group represented by $R^1$, where $R^1$ is a group selected from alkyl group, alkoxy group, halogen atom and nitro group, in the presence of a catalyst selected from Arrhenius acids and Lewis acids, thereby obtaining 3,3,3-trifluoropropionaldehyde represented by formula [2]

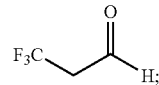

[2]

and
oxidizing the 3,3,3-trifluoropropionaldehyde with an oxidizing agent.

2. A process for producing 3,3,3-trifluoropropionic acid, as claimed in claim 1, wherein R is a phenyl group.

3. A process for producing 3,3,3-trifluoropropionic acid, as claimed in claim 1, wherein the catalyst is one selected from the group consisting of sulfuric acid, hydrochloric acid, iron (III) chloride, copper(II) chloride, aluminium chloride, tin (IV) chloride and titanium chloride.

4. A process for producing 3,3,3-trifluoropropionic acid, as claimed in claim 1, wherein the catalyst has an amount of 0.005 to 0.5 equivalent relative to the benzyl vinyl ether represented by the formula [1].

5. A process for producing 3,3,3-trifluoropropionic acid, as claimed in claim 1, wherein the benzyl vinyl ether represented by the formula [1] is produced by reacting 1-halogeno-3,3,3-trifluoropropene represented by formula [4]

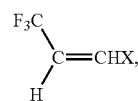

[4]

where X is a halogen selected from the group consisting of fluorine, chlorine, bromine and iodine, in the presence of a basic substance with benzyl alcohol represented by formula [5]

RCH$_2$OH   [5]

where R is one of a phenyl group and a phenyl group having a substitution group represented by $R^1$, where $R^1$ is a group selected from alkyl group, alkoxy group, halogen atom and nitro group.

6. A process for producing 3,3,3-trifluoropropionic acid, as claimed in claim 5, further comprising the steps of:
distilling off 3,3,3-trifluoropropionaldehyde represented by the formula [2] from a reaction mixture solution formed by the hydrolysis step to obtain a distillation residue;
further distilling the distillation residue, thereby collecting benzyl alcohol represented by the formula [5].

7. A process for producing 3,3,3-trifluoropropionic acid, as claimed in claim 6, wherein the oxidizing agent includes nitric acid.

* * * * *